United States Patent
Fanning

(10) Patent No.: US 10,029,954 B2
(45) Date of Patent: Jul. 24, 2018

(54) LIQUID FERTILIZER COMPOSITION CONTAINING COLOR CHANGE INDICATOR

(71) Applicant: The Andersons, Inc., Maumee, OH (US)

(72) Inventor: Barry Fanning, Sycamore, OH (US)

(73) Assignee: The Andersons, Inc., Maumee, OH (US)

( * ) Notice: Subject to any disclaimer, the term of this patent is extended or adjusted under 35 U.S.C. 154(b) by 168 days.

(21) Appl. No.: 14/725,518

(22) Filed: May 29, 2015

(65) Prior Publication Data

US 2015/0344380 A1    Dec. 3, 2015

Related U.S. Application Data

(60) Provisional application No. 62/004,577, filed on May 29, 2014.

(51) Int. Cl.

| | |
|---|---|
| C05G 1/00 | (2006.01) |
| C05G 3/00 | (2006.01) |
| C05C 9/00 | (2006.01) |
| A01N 57/20 | (2006.01) |
| C05B 7/00 | (2006.01) |
| C05C 3/00 | (2006.01) |
| C05C 7/00 | (2006.01) |
| C05G 3/02 | (2006.01) |
| C05G 3/06 | (2006.01) |
| C05B 17/00 | (2006.01) |
| C05D 9/02 | (2006.01) |
| C05C 5/04 | (2006.01) |
| C05C 11/00 | (2006.01) |
| C05C 1/00 | (2006.01) |

(52) U.S. Cl.
CPC ............ *C05G 3/0094* (2013.01); *A01N 57/20* (2013.01); *C05B 7/00* (2013.01); *C05B 17/00* (2013.01); *C05C 1/00* (2013.01); *C05C 3/00* (2013.01); *C05C 5/04* (2013.01); *C05C 7/00* (2013.01); *C05C 9/00* (2013.01); *C05C 11/00* (2013.01); *C05D 9/02* (2013.01); *C05G 1/00* (2013.01); *C05G 3/0076* (2013.01); *C05G 3/02* (2013.01); *C05G 3/06* (2013.01)

(58) Field of Classification Search
None
See application file for complete search history.

(56) References Cited

U.S. PATENT DOCUMENTS

| | | | | |
|---|---|---|---|---|
| 3,918,952 A | * | 11/1975 | Neumiller | C05B 13/06 71/28 |
| 5,019,149 A | * | 5/1991 | Hawkins | C05D 9/02 71/29 |
| 5,278,132 A | * | 1/1994 | Fisher | A01N 25/00 424/10.31 |
| 5,341,932 A | | 8/1994 | Chen et al. | |
| 5,441,713 A | * | 8/1995 | Dubin | B01D 53/56 210/697 |
| 6,241,795 B1 | * | 6/2001 | Svec | C05F 11/10 71/11 |
| 6,802,994 B1 | * | 10/2004 | Kegeler | A62D 1/0035 106/18.11 |
| 6,831,038 B2 | | 12/2004 | Volgas et al. | |
| 8,492,314 B2 | * | 7/2013 | Greyling | A01N 25/00 116/206 |
| 8,551,533 B2 | | 10/2013 | Brown et al. | |
| 2005/0022570 A1 | * | 2/2005 | Duarte-MacDonald | C05B 13/06 71/33 |
| 2005/0048665 A1 | * | 3/2005 | Bloomberg | A01N 65/00 436/166 |
| 2006/0166898 A1 | | 7/2006 | Chen | |
| 2008/0134738 A1 | * | 6/2008 | Roberts | C05C 9/02 71/30 |
| 2008/0262061 A1 | | 10/2008 | Roberts et al. | |
| 2008/0269053 A1 | * | 10/2008 | Less | C05B 7/00 504/101 |
| 2010/0154498 A1 | * | 6/2010 | Valencia | C05D 9/02 71/23 |
| 2013/0152233 A1 | | 6/2013 | Lorsbach et al. | |
| 2014/0073599 A1 | | 3/2014 | Cheung et al. | |

(Continued)

OTHER PUBLICATIONS

"Diamond-Grow Organic 100% Soluble Spray Dried Powder-95% Humic Acid" by Humic Growth Solutions, 112 Badger Park Drive, Jackonsville, Florida 32259, info@humic growthsolutions.com, pp. 1-2; Fertilizer and Lime Analysis Reporet and Non-Nutritive Metals Report, both from A&L Western Agricultural Laboratories pp. 3-4.*

(Continued)

*Primary Examiner* — Wayne Langel

(74) *Attorney, Agent, or Firm* — Avery N. Goldstein; Blue Filament Law, PLLC

(57) ABSTRACT

A liquid fertilizer adjuvant composition is provided that includes a fertilizer, a pH buffering agent, a surfactant, and one or more color indicator that produce a first color change that indicates when an pre-selected first level of field treatment has been achieved. The composition is provided as a single solution. A second color change occurs when a pre-selected second, higher level of field treatment is required. The color change indicative of a pre-selected pH, water hardness, or a combination of both. The composition is particular well suited for inclusion of a urea fertilizer.

11 Claims, No Drawings

(56) References Cited

U.S. PATENT DOCUMENTS

2015/0218060 A1* 8/2015 Hayes .................. C05G 3/08
　　　　　　　　　　　　　　　　　　　　71/28
2016/0340267 A1* 11/2016 Hayes .................. C05G 3/0041

OTHER PUBLICATIONS

U, cont. OMRI Listed Certificate, p. 5; Material Registration Certificate issued to North American Trading Group, Inc. dba Humic Growth Solutions from the Department of Agriculture, p. 6; two Attestations issued to Humic Growth Solutions from Ecocert, pp. 7-8; Material Safety Data Sheet, pp. 9-11.*

* cited by examiner

LIQUID FERTILIZER COMPOSITION CONTAINING COLOR CHANGE INDICATOR

RELATED APPLICATIONS

This application is a non-provisional application that claims priority benefit of U.S. Provisional Application Ser. No. 62/004,577 filed May 29, 2015; the contents of which are hereby incorporated by reference.

FIELD OF THE INVENTION

The present invention in general relates to liquid fertilizer and in particular to an improved liquid fertilizer composition containing a color change indicator.

BACKGROUND OF THE INVENTION

The application of liquid fertilizers typically involves the combination of several products with water in a spray tank in order to minimize the number of trips needed to treat a crop. These mixtures usually include a substantial amount of water with several gallons of various fertilizers, herbicides, insecticides, etc. A critical concern is the compatibility of all the components in the mixture, where the components need to blend without physical issues (e.g., precipitation, phase separation, foaming) at expected efficacy levels. Adjuvants (water conditioners, surfactants, pH control agents, etc.) are often added to enhance physical compatibility, maintain efficacy, or enhance delivery efficiency. Two, three, or four of these efficiency enhancing adjuvants are often added to one tank mix. Furthermore, some treatments require testing to determine proper dosing. All of this requires time, effort and management of inventory.

Thus there exists a need for a premixed liquid fertilizer adjuvant with indicators for proper dosing for a particular application.

SUMMARY OF THE INVENTION

A liquid fertilizer adjuvant composition is provided that includes a fertilizer, a pH buffering agent, a surfactant, and one or more color indicator that produce a first color change that indicates when an pre-selected first level of field treatment has been achieved. The composition is provided as a single solution. A second color change occurs when a pre-selected second, higher level of field treatment is required. The color change indicative of a pre-selected pH, water hardness, or a combination of both. The composition is particular well suited for inclusion of a urea fertilizer. Specific color change indicators include: 2-(N,N-Dimethyl-4-aminophenyl)azobenzenecarboxylic acid, 2-bromo-6-methylphenol, 3',3",5',5"-tetrabromophenolsulfonphthalein, 3,3',5,5'-Tetrabromo-m-cresolsulfonphthalein, 3,3-bis(4-hydroxy-2-methyl-5-propan-2-ylphenyl)-2-benzofuran-1-one, 3,3-bis(4-hydroxynaphthalen-1-yl)-2-benzofuran-1-one, 3,3-bis(4-hydroxyphenyl)isobenzofuran-1 (3H)-one, 3-Amino-7-dimethylamino-2-methylphenazine hydrochloride, 4,4'-(1,1-dioxido-3H-2,1-benzoxathiole-3,3-diyl)bis(2-bromo-6-isopropyl-3-methylphenol), 5-[(p-nitrophenyl)azo] salicylic acid sodium salt, azolitmin, disodium 4-amino-3-[4-[4-(1-amino-4-sulfonato-naphthalen-2-yl) diazenylphenyl]phenyl]diazenyl-naphthalene-1-sulfonate, erythrolitmin, hexamethyl pararosaniline chloride, leucazolitmin, leucoorcein. o-cresolsulfonephthalein, p-dimethylaminoazobenzene, phenolsulfonphthalein, sodium 4-[(4-dimethylamino)phenyldiazenyl]benzenesulfonate, and spaniolitmin, thymolsulphonephthalein. A method is also provided for the application of the composition in concert with an herbicide, pesticide, fungicide, or plant growth regulator to growing plants.

DETAILED DESCRIPTION OF THE PREFERRED EMBODIMENTS

The present invention has utility as a premixed liquid fertilizer adjuvant composition that combines pH adjustment, water treatment, and surfactants into a single product that has a color change that indicates when the appropriate level of treatment has been achieved, with an additional color change that indicates a higher level of treatment for when a more aggressive approach is required for an application. Embodiments of the inventive liquid fertilizer adjuvant composition provide a convenient single solution to address of prior liquid fertilizer treatments that required testing to determine proper dosing and that required time, effort, and management of inventory of the constituent parts.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

The fertilizer illustratively includes a variety of soluble compositions enhancing the N-P-K value by more than 1 unit of nitrogen, phosphorus, or potassium. Fertilizers operative herein illustratively include ammonia sulfate, an ammonia salt of a carboxylic acid, mono- or di-potassium phosphate, a micronutrient, ammonia nitrate, urea, ammonia citrate, ammonia acetate, dicyandiamide, crotilidiene diurea, nitrocellulose, metal ammonium phosphates, ammonium sulfate, coated urea, monoammonium phosphate, diammonium phosphate, calcium nitrate, isobutylidene diurea, or combinations thereof. Typical amounts of each fertilizer range from 1 to 40 total weight percent, with a total weight of fertilizer being between 1 to 50%.

In addition to fertilizers, an inventive composition illustratively includes micronutrients such as calcium, magnesium, boron, zinc, copper, iron, sulfur, or combinations thereof. Typical amounts of each fertilizer range from 0.1 to 10 total weight percent, with a total weight of fertilizer being between 1 to 20% micronutrients.

Additionally, a buffering agent is added to the composition to reduce the pH. A buffering agent illustratively including mineral acids such as sulfuric acid, sulfonic acid, sulfurous acid, nitric acid, or nitrous acid; an organic acid such as glutaric acid, gluconic acid, lactic acid, glycolic acid, acrylic acid, or combinations thereof. A buffering agent is provided to typically adjust the composition pH to between 4 and 7.

Herbicides, pesticides fungicides and plant growth regulators that respond very favorably to pH adjustment illustratively include ALIETTE® (Aluminum tris(O-ethyl phosphonate), APOLLO® (clofentizine), Azinphos-Methyl, BENLATE® (benomyl), BIOPROTEC® *Bacillus thuringiensis* subspecies kurstaki), captan, CARZOL® (Formetanate hydrochloride), COMMAND® (comazone), CYGON® (dimethoate), CYMBUSH® (beta-cypermethrin), DIPEL® (ACTIVE INGREDIENT: *Bacillus thuringiensis*, subsp. kurstaki, strain ABTS-351, fermentation solids, spores, and insecticidal toxins), ETHREL® (ethephon), FORAY® *Bacillus thuringiensis* subsp. kurstaki strain ABTS-351), FURADAN® (Carbofuran), GLYFOS® (glyphosate as a isopropylamine salt), Glyphosate, GUTHION® (azinphosmethyl), HORIZON® (2-propynyl-(R)-2-[4-(5-chloro-3-fluoro-2-pyridyloxy)-phenoxy]-propionate), IMIDAN® (phosmet), KELTHANE® (dicofol), LAGON® (dimethoate), malathion, OMITE® (propargite), phosphamidon, POAST® (sethoxydim), ROUNDUP® (potassium glyphosate), ROVRAL® (iprodione), SEVIN® (carbaryl), SNIPER® (bifenthrin), THIODAN® (endosulfan) VECTO-BAC® (*Bacillus thuringiensis*, subsp. *israelensis*, strain AM65-52), and VYDATE® (oxamyl). The inventive composition is readily applied prior to delivering one of the aforementioned herbicides, pesticides, fungicides, or plant growth regulators to growing plants. In certain embodiments, the inventive composition is pre-mixed with the herbicides, pesticides, fungicides, or plant growth regulators prior to application to the growing plants.

Embodiments of an inventive liquid fertilizer adjuvant also include a surfactant. A surfactant operative herein illustratively includes polysaccharides, ethylene oxide-propylene oxide mixed copolymer, alkylphenol ethoxylates, sorbitan fatty acid ester, polyethoxylated derivative of a sorbitan fatty acid ester, a fatty acid alkanolamide, silicone surfactants, ethoxylated fatty, alkyl ethoxylates, alkylphenol, polypropylene glycols, tristyrylphenol alkoxylates, amine ethoxylates, N-Acyl sarcosines, N-Acyl sarcosinate salts, alkylaryl polyethoxy carboxylate ester, tristyrylphenol alkoxylate carboxylate esters, alkylpolyglucosides, oxirane, polymers with oxirane functionality, monobutyl ether, neutralized polyacrylic acid, neutralized acrylic and methacrylic acid copolymers, propylene glycol trisiloxane, alkylphenol ethoxylates or a combination thereof. With respect to ethylene oxide-propylene oxide mixed copolymers, molecular weights are calculated as being between 500 or 75000 molecular weight. In specific inventive embodiments, an end capped EO/PO copolymer is used. Typical amounts of each surfactant range from 10 to 80 total weight percent, with a total weight of surfactant being between 1 to 50%.

Embodiments of the liquid fertilizer adjuvant composition have one or more color indicators that can be used individually or in combination to give a broader range of response with a wider variety of colors.

Color indicators used in embodiments of the inventive liquid fertilizer adjuvant composition include: 2-(N,N-Dimethyl-4-aminophenyl)azobenzenecarboxylic acid, 2-bromo-6-methylphenol, 3',3",5',5"-tetrabromophenolsulfonphthalein, 3,3',5,5'-Tetrabromo-m-cresolsulfonphthalein, 3,3-bis(4-hydroxy-2-methyl-5-propan-2-ylphenyl)-2-benzofuran-1-one, 3,3-bis(4-hydroxynaphthalen-1-yl)-2-benzofuran-1-one, 3,3-bis(4-hydroxyphenyl) iso benzofuran-1 (3H)-one, 3-Amino-7-dimethylamino-2-methylphenazine hydrochloride, 4,4'-(1,1-dioxido-3H-2,1-benzoxathiole-3,3-diyl)bis(2-bromo-6-isopropyl-3-methylphenol), 5-[(p-nitrophenyl)azo] salicylic acid sodium salt, azolitmin, disodium 4-amino-3-[4-[4-(1-amino-4-sulfonato-naphthalen-2-yl) diazenylphenyl]phenyl]diazenyl-naphthalene-1-sulfonate, erythrolitmin, hexamethyl pararosaniline chloride, leucazolitmin, leucoorcein. o-cresolsulfonephthalein, p-dimethylaminoazobenzene, phenolsulfonphthalein, sodium 4-[(4-dimethylamino)phenyldiazenyl]benzenesulfonate, spaniolitmin, Chromatint 2089 liquid, Chromatint Blue 2090, Chromatint Red 2091, or o-Cresolsulfonephthalein, thymolsulphonephthalein. Typical amounts of each color indicator range from 0.5 ppm to 1% total weight percent, with a total weight of color indicators being between 0.5 ppm to 2%.

Additional additives that are readily provided in embodiments of the liquid fertilizer adjuvant illustratively include an anti-corrosion agent, anti-caking agents, stabilizers, anti-freezes, anti-foam agents, sticking agents, spreading agents, wetting agents, drift control agents, complexing agents, softening agents, and mixtures thereof and the like. Typical amounts of each additive range from 0 to 30 total weight percent, with a total weight of additive being between 0 to 50%.

In specific inventive embodiments, the molar ratio of fertilizer:(buffering agent):color indicator are held constant when the fertilizer:buffering agent are urea and sulfuric acid. In specific embodiments, the surfactant is an ethylene oxide/propylene oxide (EP/PO) copolymer that is present at between 15 and 30 total weight percent to achieve optimal droplet spreading.

A summary of the typical ranges for an inventive liquid fertilizer are provided in the following Table 1.

TABLE 1

Typical ranges of inventive liquid fertilizer formulation in total weight percentages include:

| Component | Total weight % |
| --- | --- |
| water | Remainder |
| fertilizer | 0 to 40% |
| buffering agent | to pH 1 to 5 |
| surfactants | 5 to 30% |
| coloring agents | 0.0005 to 2% |
| additives | 0.01 to 10% |

EXAMPLES

Example 1

An optimal composition where all performance parameters is provided with an unusually high efficacy:

| Component | Total weight percent |
| --- | --- |
| Water | Remainder |
| Sulfuric acid | 8 |
| Urea prill | 30 |
| polyalkylene glycol surfactant | 20 |
| Bromocresol green - sodium salt | 0.015 |

Example 2

The series of compositions are formulated with various surfactants including: polysaccharides, medium molecular weight EO/PO copolymer, High molecular weight EO/PO copolymer, endcapped high molecular weight EO/PO copolymer, endcapped medium molecular weight EO/PO copolymer, endcapped low molecular weight EO/PO copolymer, alkylphenol ethoxylates, and polyacrylates in place of polyalkylene glycols with similar results.

| Component | Total weight percent |
| --- | --- |
| Water | Remainder |
| Sulfuric acid | 8 |
| Urea prill | 30 |
| Surfactant* | 20 |
| Bromocresol green - sodium salt | 0.015 |

*Surfactants used in each individual composition A) polyacrylic acid B) alkylphenol ethoxylate C) alkyl ethoxylate D) polyalkylene glycol E) polysaccharide F) polycarboxylate ester

Example 3

The composition in Example 1 is also tried with various indicator dyes including: 2-(N,N-Dimethyl-4-aminophenyl)azobenzenecarboxylic acid, 2-bromo-6-methylphenol, 3',3",5',5"-tetrabromophenolsulfonphthalein, 3,3',5,5'-Tetrabromo-m-cresolsulfonphthalein, 3,3-bis(4-hydroxy-2-methyl-5-propan-2-ylphenyl)-2-benzofuran-1-one, 3,3-bis(4-hydroxynaphthalen-1-yl)-2-benzofuran-1-one, 3,3-bis(4-hydroxyphenyl)isobenzofuran-1(3H)-one, 3-Amino-7-dimethylamino-2-methylphenazine hydrochloride, 4,4'-(1,1-dioxido-3H-2,1-benzoxathiole-3,3-diyl)bis(2-bromo-6-isopropyl-3-methylphenol). Each at an amount of 0.015 total weight percent with similar results.

Example 4

Glyphosate works most effectively when plants are actively growing. Fall chemical applications are especially challenging because of the slowed plant metabolism rates in these cold, wet conditions. In an actual field trial using label rates of glyphosate in treated water test users have reported exceptional herbicide activity under these very demanding conditions. While previous experience would have indicated a slow response affecting mainly the most susceptible plant species the application utilizing this invention surprisingly gave a rapid response for complete 'burn down', obvious weed mortality across all susceptible species.

The foregoing description is illustrative of particular embodiments of the invention, but is not meant to be a limitation upon the practice thereof. The following claims, including all equivalents thereof, are intended to define the scope of the invention.

The invention claimed is:

1. A liquid fertilizer adjuvant composition, said composition consisting essentially of:
    a liquid fertilizer present from 10 to 50 total weight percent and dissolved in water;
    a pH buffering agent present in an amount to achieve a pH of 1 to 5 and distinct from said liquid fertilizer;
    one or more surfactants;
    one or more color indicators present in an amount sufficient to indicate a color change when a pre-selected level of treatment has been achieved, the one or more color indicators being selected from the group consisting of: 2-(N,N-Dimethyl-4-aminophenyl)azobenzenecarboxylic acid, 2-bromo-6-methylphenol, 3',3",5',5",tetrabromophenolsulfonphthalein, 3,3',5,5'-Tetrabromo-m-cresolsulfonphthalein, 3,3-bis(4-hydroxy-2-methyl-5-propan-2-ylphenyl)-2-benzofuran-1-one, 3,3-bis(4-hydroxynaphthalen-1-yl)-2-benzofuran-1-one, 3,3-bis(4-hydroxyphenyl)isobenzofuran-1(3H)-one, 3-Amino-7-dimethylamino-2-methylphenazine hydrochloride, 4,4'-(1,1-dioxido-3H-2,1-benzoxathiole-3,3-diyl)bis(2-bromo-6-isopropyl-3-methylphenol), 5-[(p-nitrophenyl)azo]salicylic acid sodium salt, azolitmin, disodium 4-amino-3-[4-[4-(1-amino-4-sulfonato-naphthalen-2-yl)diazenylphenyl]phenyl]diazenyl-naphthalene-1-sulfonate, erythrolitmin, hexamethyl pararosaniline chloride, leucazolitmin, leucoorcein, o-cresolsulfonephthalein, p-dimethylaminoazobenzene, phenolsulfonphthalein, sodium 4-[(4-dimethylamino)phenyldiazenyl]benzenesulfonate, spaniolitmin, and thymolsulphonephthalein;
    said composition premixed as a liquid applicable for field treatment; and
    optionally including at least one of: one or more micronutrients, an anti-corrosion agent, an anti-caking agent, a stabilizer, an anti-freeze, an anti-foam agents, a sticking agent, a spreading agent, a wetting agent, a drift control agent, a complexing agent, or a softening agent; and
    the liquid fertilizer, the pH buffering agent, the one or more surfactants, and the one or more color indicators blendable with water without a physical issue of phase separation or precipitation at the pre-selected level of treatment.

2. The composition of claim 1 wherein said one or more color indicators is at least two color change indicators wherein the second color is present in an amount sufficient to indicate a second efficacy level.

3. The composition of claim 1 wherein said one or more surfactants is one or more of: oxirane, methyl-, polymer with oxirane, monobutyl ether, neutralized polyacrylic acid, neutralized acrylic and methacrylic acid copolymers, propylene glycol trisiloxane, or alkylphenol ethoxylates.

4. The composition of claim 1 wherein said fertilizer is urea.

5. The composition of claim 1 wherein said fertilizer is one or more of: ammonia sulfate, an ammonia salt of a carboxylic acid, mono- or di-potassium phosphate, ammonia nitrate, ammonia citrate, ammonia acetate, dicyandiamide, crotilidiene diurea, nitrocellulose, metal ammonium phosphates, ammonium sulfate, coated urea, monoammonium phosphate, diammonium phosphate, calcium nitrate, or isobutylidene diurea.

6. The composition of claim 1 wherein said buffering agent is sulfuric acid.

7. The composition of claim 1 wherein said one or more micronutrients is one of: calcium, magnesium, boron, zinc, copper, iron, or sulfur.

8. The composition of claim 1 wherein said one or more surfactants is an ethylene oxide/propylene oxide copolymer present at between 15 and 30 total weight percent.

9. A method of treating growing plants comprising:
    applying the composition of claim 1 to the growing plants; and
    delivering at least one of an herbicide, a pesticide, or a fungicide to the growing plants in concert with the composition.

10. The method of claim 9 wherein the composition and said at least one of said herbicide, said pesticide, or said fungicide are premixed prior to said applying.

11. The method of claim 9 wherein said herbicide is present and is a glyphosate.

* * * * *